United States Patent [19]

Curtis et al.

[11] Patent Number: 4,605,751

[45] Date of Patent: Aug. 12, 1986

[54] BIMETALLIC CLUSTER CATALYSTS

[75] Inventors: M. David Curtis; Johannes W. Schwank; Levi T. Thompson; P. Douglas Williams, all of Ann Arbor, Mich.

[73] Assignee: The Board of Regents Acting For and On Behalf of the University of Michigan, Ann Arbor, Mich.

[21] Appl. No.: 572,201

[22] Filed: Jan. 17, 1984

[51] Int. Cl.[4] .................... C07F 11/00; C07F 15/02
[52] U.S. Cl. .................................. 556/29; 556/30; 502/152; 518/714
[58] Field of Search ...... 260/429 R, 429 CY, 439 CY

[56] References Cited

U.S. PATENT DOCUMENTS

| | | | |
|---|---|---|---|
| 4,000,172 | 12/1976 | Fachinetti et al. | 260/429 CY |
| 4,039,566 | 8/1977 | Fachinetti et al. | 260/429 CY X |
| 4,124,647 | 11/1978 | McVicker | 260/429 CY X |
| 4,138,420 | 2/1979 | Unruh et al. | 260/429 CY X |
| 4,199,520 | 4/1980 | Cosby et al. | 260/429 R |
| 4,320,064 | 3/1982 | Vidal | 260/429 R |
| 4,349,521 | 9/1982 | Shore et al. | 260/429 R X |
| 4,349,522 | 9/1982 | Shore et al. | 260/439 CY X |
| 4,481,375 | 11/1984 | Kalk et al. | 260/429 R X |

OTHER PUBLICATIONS

Klinger et al., J.A.C.S. 97(12), pp. 3535–3536 (1975).

*Primary Examiner*—Helen M. S. Sneed
*Attorney, Agent, or Firm*—Head, Johnson & Stevenson

[57] ABSTRACT

A facile synthesis of the precursor, $Cp_2Mo_2(\mu\text{-}S)_2(\mu\text{-}SH)_2$, to novel heterobimetallic cluster compositions (e.g., $Cp_2Mo_2Fe_2(\mu\text{-}S)_2(CO)_8$; $Cp_2Mo_2Ni_2(\mu_3\text{-}S)_4(CO)_2$; $Cp_2Mo_2Co_2(\mu_3\text{-}S)_2(\mu_4\text{-}S)(CO)_4$; $Cp_2Mo_2Fe_2(\mu_3\text{-}S)_4(CO)_6$ and $Cp_4Mo_2Ni_2S_4$ and the subsequent synthesis and use of the heterobimetallic cluster compositions as highly active and selective catalysts for the hydrogenation of carbon monoxide. Such heterobimetallic cluster catalysts supported on alumina exhibit extraordinary activity and selectivity with respect to the formation of ethane without concomitant formation of $C_3$, $C_4$ and heavier hydrocarbons. The catalysts are contemplated as being useful for syngas conversion even in the presence of several ppm of $H_2S$ or the like in the feedstream.

16 Claims, 9 Drawing Figures

BIMETALLIC CLUSTER CATALYSTS

BACKGROUND OF THE INVENTION
1. Field of the Invention

This invention relates to the preparation of novel cluster complexes and their use as highly active and selective catalysts. More specifically, the present invention relates to the synthesis of bimetallic clusters of Cr, Mo or W with Fe, Co or Ni and their use as catalysts for hydrogenation of carbon monoxide.

2. Description of the Prior Art

In general, previously known catalysts for hydrogenation of carbon monoxide are selective for $C_1$ compounds only (such as $CH_4$ or $CH_3OH$) and non-selective with respect to high carbon number compounds producing complex mixtures. Since many of the components of such mixtures have either low commercial value or undesirable properties, they must be separated from the more desirable products to achieve commercial significant products. However, the necessary separation steps are costly and inconvenient.

With the prospects of syngas derived fuels and feedstocks as alternate hydrocarbon sources, whether from reformed methane or coal gasification, it is anticipated that chemistry based on CO and $H_2$ will eventually replace petroleum as a source of chemical feedstocks and fuels. However, major problems exist with respect to syngas conversion processes including sulfur poisoning of the catalyst and lack of selectivity. For example, both methanation catalysts based on Ni and common Fisher-Tropsch (F.-T.) catalysts are extremely sensitive to poisoning by sulfur in the syngas feed stream as are the ZnO/Cu methanol synthesis catalysts. Therefore, the development of selective, sulfur-tolerant catalysts for syngas conversion is needed.

In general, metal sulfides (see; Mitchell, Catalysis (London) 1977, 1, 204–233) are known as catalysts and, in particular, iron-molydbenum-sulfur compounds and the like based on "sulfided " metal molybdates on oxide supports (see, Furimsky, Catal. Rev.-Sci. Eng. 1980, 22, 371 and DuBois et al J. Am. Chem. Soc. 1979, 101, 5245; Ibid 1980, 102, 7456) are suggested as possible hydrodesulfurization catalysts and (see; Coucouvanis et al, Acc. Chem. Res. 1981, 14, 20 and Muller et al, Angew. Chem., Int. Ed. Engl. 1981, 20, 934) as the nitrogenase cofactor. It is also generally known and reported (see; Vahrenkamp, Angew. Chem., Int. Ed. Engl. 1975, 14, 322) that the presence of sulfur ligands tend to stabilize metal clusters.

However, the typical heterobimetallic sulfur containing catalysts of the prior art (e.g., CoMoS system) is prepared either by coprecipitation or by sequential or simultaneous absorption of the metals (e.g., $Co(NO_3)_2$ and ammonium heptamolybdate) on $Al_2O_3$, followed by calcining and sulfidation. Prepared in this manner, the catalysts contain varying proportions of inactive metal (e.g., Co) in the oxide support, as well as in the active CoMoS phase and at high loading inactive metal sulfides (e.g., $Co_9S_8$). Hence, it has been impossible to establish even the stoichiometry of the active phase. Further, prior to the present invention, the lack of a practical method for the synthesis of $Cp_2Mo_2(\mu-S)_2(\mu-SH)_2$ has prevented the investigation and synthesis of cluster compounds based on this intermediate composition.

SUMMARY OF THE INVENTION

In view of the prior art, we have discovered a novel class of heterobimetallic cluster compositions and methods of synthesis which incorporate an early transition metal such as Cr, Mo or W; a late transition metal such as Fe, Co or Ni; and sulfur in a discrete molecular cluster of known stoichiometry and initial structure. These discrete molecular clusters when dissolved in an appropriate solvent, absorbed onto the surface of a refractory support such as alumina, silica gel, or carbon and then subsequently dried and subjected to thermolysis at about 50° to about 500° C. in an inert or reducing atmosphere (e.g., He, $N_2$ or $H_2$) result in compositions which are useful as highly active and selective catalysts for the hydrogenation of carbon monoxide.

Thus, the novel heterobimetallic cluster compositions provided according to the instant invention are characterized by the formula $Cp_2M_2M_2''S_x(CO)_n$ wherein $Cp=\eta^5-C_5H_4R$ and R is $-CH_3$ or $-H$ and wherein M is a metal selected from the group consisting of Mo, W and V and wherein M' is a metal selected from the group consisting of Fe, Co and Ni and x and n are integers from about 2 to about 8 which specifically include the heterobimetallic cluster compositions selected from the group consisting of: $Cp_2Mo_2Fe_2(\mu-S)_2(CO)_8$; $Cp_2Mo_2Ni_2(\mu_3-S)_4(CO)_2$; $Cp_2Mo_2Co_2(\mu_3-S)_2(\mu_4-S)(CO)_4$; $Cp_2Mo_2Fe_2(\mu_3-S)_4(CO)_6$ and $Cp_4Mo_2Ni_2S_4$.

The hydrogenation catalysts compositions according to the present invention comprise the above novel heterobimetallic cluster compositions supported on a refractory selected from the group consisting of alumina, silica gel and carbon and preferably activated by heating the catalyst composition in the presence of hydrogen, helium, nitrogen or a mixture thereof.

The novel method of synthesizing the precursor, $Cp_2Mo_2(\mu-S)_2(\mu-SH)_2$, to the novel heterobimetallic cluster compositions according to the present invention comprises the steps:

(a) chemically reducing the polymeric sulfide $(Cp_2Mo_2S_x)_n$ dissolved in an organic solvent with a chemical reducing agent;

(b) quenching the reduction reaction by the addition of water;

(c) stripping the excess solvent and water; and (d) recovering $Cp_2Mo_2(\mu-S)_2(\mu-SH)_2$ wherein $Cp=\eta^5-C_5H_4R$ and R is $-CH_3$ or $-H$.

Preferably according to the invention, the synthesis of $Cp_2Mo_2(\mu-S)_2(\mu-SH)_2$ is accomplished by a final water washing and purifying step. The preferred organic solvent is tetralhydrofuran, THF, and the preferred reducing agent is triethyl lithium borohydride, $LiEt_3BH$.

Thus, the method of preparing a molybdenum heterobimetallic cluster composition according to the instant invention comprises the steps of:

(a) reacting $Cp_2Mo_2(\mu-S)_2(\mu-SH)_2$ where $Cp=\eta^5-C_5H_4R$ and $R=-CH_3$ or $-H$ with a group 8 metal carbonyl selected from the group consisting of $Ni(CO)_4$, $Co_2(CO)_8$, $Fe_2(CO)_9$ and $Cp_2Ni_2(CO)_2$; and (b) recovering a heterobimetallic cluster composition selected from the group consisting of $Cp_2Mo_2Ni_2(\mu_3-S)_4(CO)_2$, $Cp_2Mo_2Co_2(\mu_3-S)_2(\mu_4-S)(CO)_4$, $Cp_2Mo_2Fe_2(\mu_3-S)_4(CO)_6$ and $Cp_4Mo_2Ni_2S_4$ or the steps of:

(a) reacting $Cp_2Mo_2(CO)_4$ where $Cp=\eta^5-C_5H_4R$ where R is $-CH_3$ or $-H$ with $Fe_2S_2(CO)_6$; and (b) recovering a heterobimetallic cluster composition $Cp_2Mo_2Fe_2(\mu\text{-}S)_2(CO)_8$.

And, the method for catalytic hydrogenation of carbon monoxide according to the present invention comprises the step of chemically reacting carbon monoxide and hydrogen in the presence of one or more of the above recited catalyst compositions.

It is an object of the instant invention to provide novel heterobimetallic cluster complexes and a facile method of synthesizing precursors to the cluster complexes. It is a further object to provide a highly active and selective catalyst for hydrogenation of carbon monoxide based on these cluster complexes. It is an additional object to provide heterobimetallic cluster compositions that are stabilized by the presence of sulfido bridging and to provide sulfurtolerant, syngas catalysts therefrom. And, it is an object of the present invention to provide catalysts based on discrete molecular compositions resulting in fixed metallic ratios in the final catalytic composition. Fulfillment of these objects and the presence and fulfillment of other objects will be apparent upon complete reading of the specification and claims taken in conjunction with the attached drawing.

DESCRIPTION OF THE PREFERRED EMBODIMENTS

Figure 1:
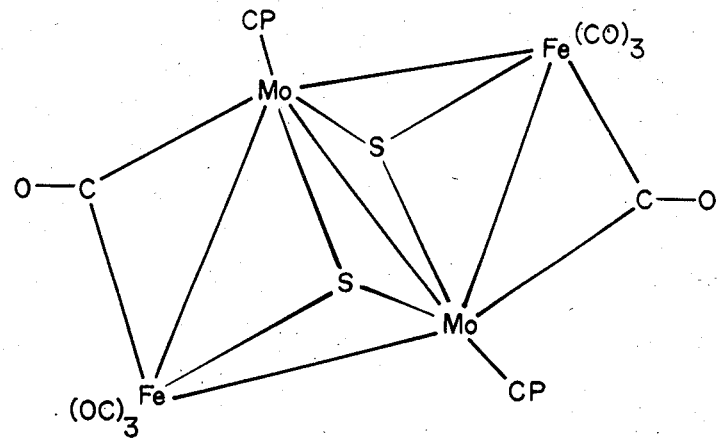
FIGS. 1 through 6 illustrate the molecular structure of the heterobimetallic clusters according to the instant invention.

The heterobimetallic cluster complexes and catalyst systems of the instant invention are composed of and derived from discrete clusters of known stoichiometry and initial structure. As such, the invention provides a rational and controlled method for the synthesis of cluster compounds containing an early transition metal (e.g., Mo, V or W), a late transition metal (e.g., Fe, Co or Ni) and sulfur. Under the reaction conditions of the instant invention, as exemplified later, sintering of the catalyst and support will be minimized, and the catalytically active sites will be well separated, molecular clusters of known metal to metal ratios. Because the novel catalysts contain late transition metals, early transition metals and sulfur directly bonded into discrete, molecular clusters, the synergistic effect of the late transition metal promoter with the other metal along with the sulfur stabilization leads to high activity, sulfur-tolerance and high selectivity. Because of the selectivity, the catalysts based on the heterobimetallic cluster complexes of the present invention lack the coking and formation of high molecular weight waxes characteristic of the Mo-catalysts of the F. T. technology. Hence, costs associated with running a water gas-shift reactor in commercial applications is eliminated.

In order to exemplify and to more fully understand and explain the rational synthesis of the bimetallic sulfided clusters according to the instant invention and to more fully illustrate the structure and stoichiometry, reference to the following reactions and figures of the drawing is appropriate. In presenting the preferred embodiments illustrated in the following reactions and the referenced figures, the $Cp=\eta^5\text{-}C_5H_4R$ where R is either a $-CH_3$ or $-H$ equation (1) is representative of the first of two overall reactions for the synthesis of the desired cluster compounds wherein the metal-metal multiple bond (i.e., the Mo-Mo triple bond) of the Cp metal carbonyl complex (i.e., $Cp_2Mo_2(CO)_4$ reacts with a metal sulfido-carbonyl complex (i.e., $Fe_2S_2(CO)_6$) to form in this case a pair of isomeric clusters as follows:

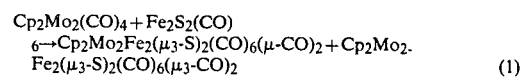

(1)

Figure 2:
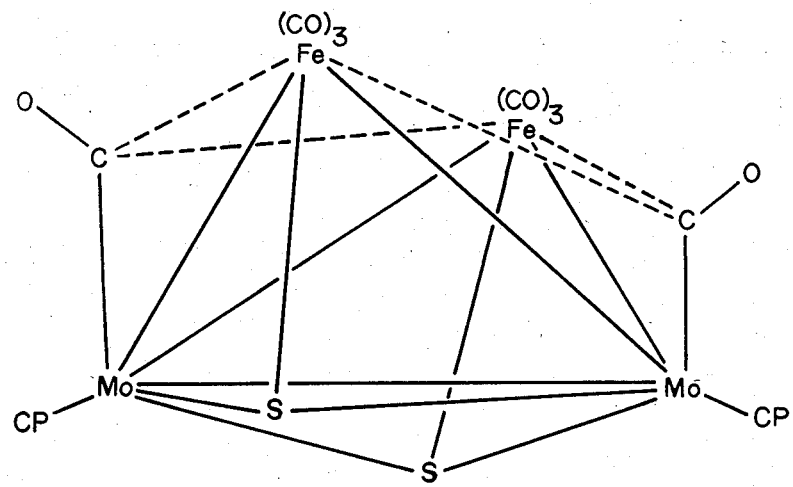

The above reaction can be performed at room temperature in toluene as the solvent resulting in essentially a quantitative yield of $Mo_2Fe_2S_2$ clusters in less than half an hour. The mixture of the isomers precipitate as dark brown, air stable crystals which are separated on a Florisil column with $CH_2Cl_2$ as the eluant. FIGS. 1 and 2 illustrate the molecular structure of each isomer. The first isomer, FIG. 2, possesses the butterfly geometry expected of a 62-electron cluster, while the second cluster, FIG. 1, has been confirmed to be a centrosymmetric configuration with a planar $Mo_2Fe_2$ skeleton.

The second overall reaction for synthesis of the desired cluster compounds involves the reaction of a late transition metal carbonyl complex with an early transition metal sulfido-sulfhydryl complex such as $Cp_2Mo_2(\mu\text{-}S)_2$. Since no convenient method of synthesis of this complex was known, the instant invention further provides such a method involving the reduction of the readily available polymeric sulfide $(Cp_2Mo_2S_x)_n$ as follows:

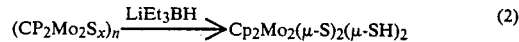

(2)

In synthesizing the cluster complex precursor, reaction 2 is allowed to proceed for several hours in THF as the solvent consuming approximately 11 equivalents of $LiEt_3BH$ per gram of polymeric sulfide. The mixture is then carefully quenched with water and the THF stripped out of the mixture. The solid is filtered and washed with water until the washings are colorless. The dried solid is then extracted with $CH_2Cl_2$ to give a deep purple solution. Removal of the $CH_2Cl_2$ gives pure $Cp_2Mo_2(\mu\text{-}S)_2(\mu\text{-}SH)_2$ as black crystals (yield 75% based on Mo used to prepare the polymeric sulfide starting material).

According to the second reaction scheme for synthesis of the heterobimetallic cluster compositions, the hydrosulfide complex formed in the reaction (2) reacts rapidly (i.e., ca 2 hours) at room temperature with a transition metal carbonyl as exemplified in reactions 3 through 6 as follows:

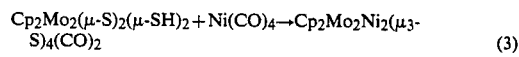

(3)

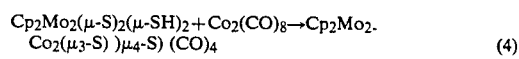

(4)

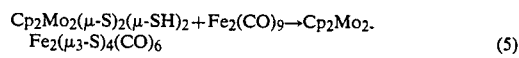

(5)

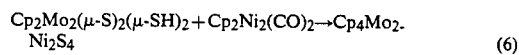

(6)

Figure 3:
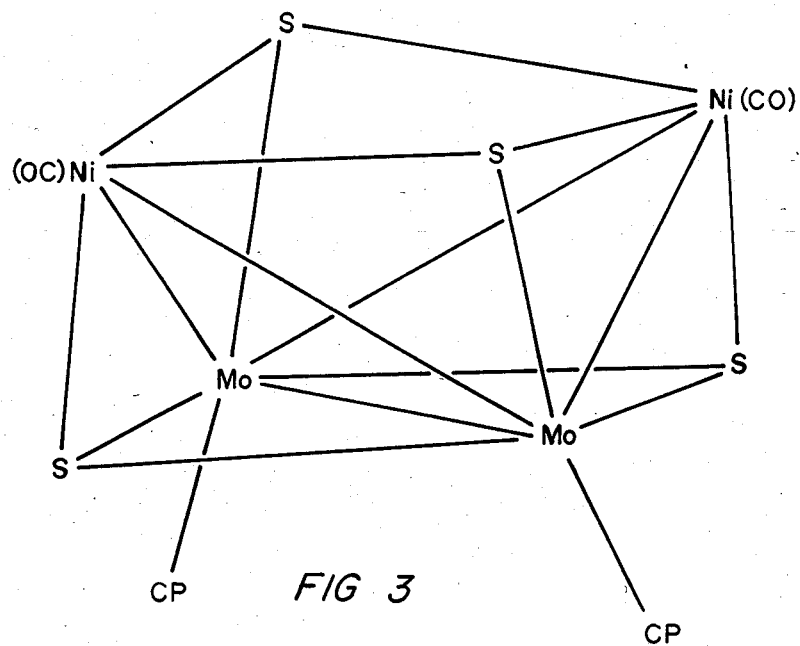
Figure 4:
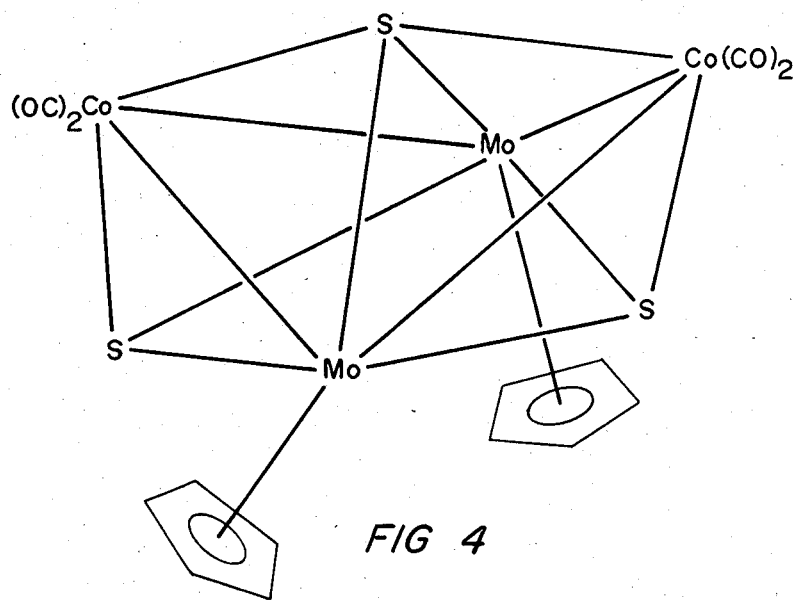
Figure 5:
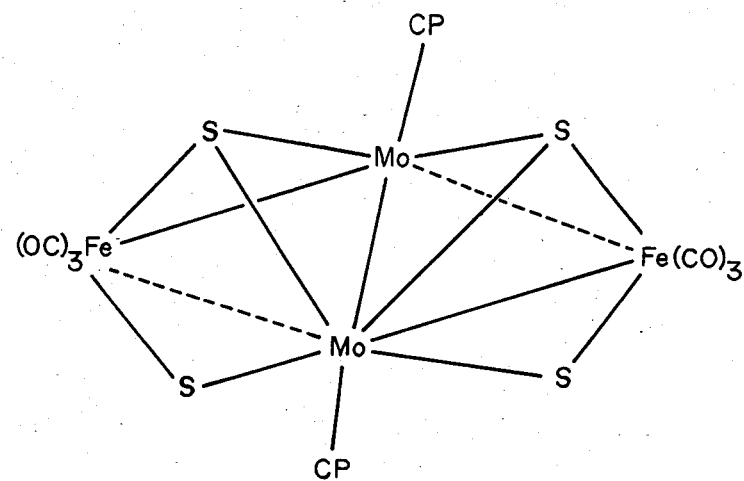
Figure 6:
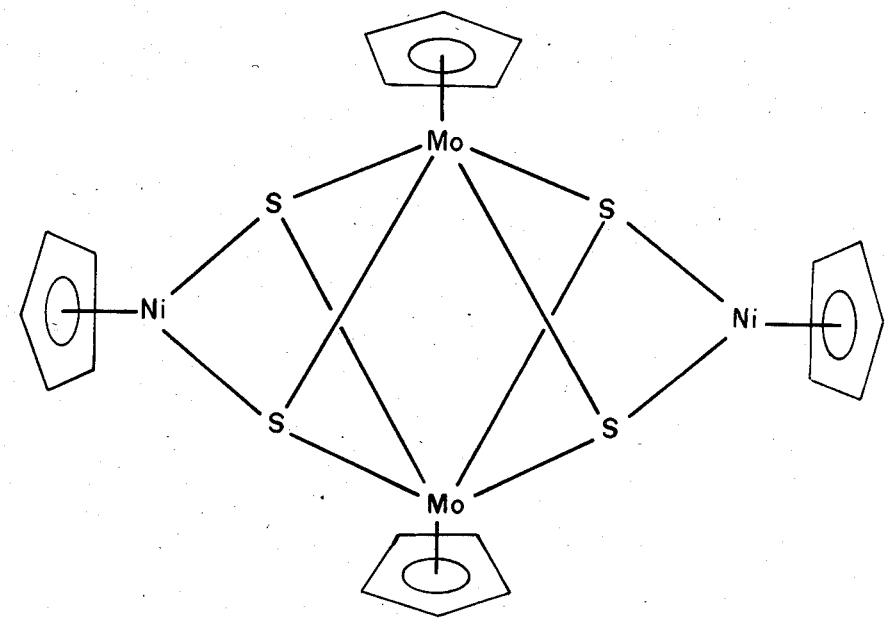

The reaction products were isolated by elution chromatography over alumina. In each case, the initial band contained the cluster. The eluant, color, and yield for reaction products 4 through 6 are typically as follows: $CH_2Cl_2$, pine green, 25%; hexane/toluene (4:1), black, 50% and $CH_2Cl_2$, emerald green, 20%. All of the cluster compounds produced in reactions 3 through 6 have been characterized by elemental and spectroscopic analysis and have been shown by single crystal X-ray crystallography to consist of discrete, molecular clusters bound together by metal-metal and metal-sulfur bonds. The corresponding structure of each are illustrated in FIGS. 3 through 6. As shown in FIG. 3, the MoNiS cluster is a cubane structure with five metal-metal bonds having 62 cluster framework electrons in the butterfly configuration with Ni at the wing tips. The MoCoS cluster of FIG. 4 contains a relatively rare $\mu_4$-S ligand in bicapped-trigonal-bipyramidal structure with high connectivity for Mo. The MoFeS cluster of FIG. 5 is centrosymmetric with two nonbonding (3.612 Å) and two bonding (2.853 Å) Mo=Fe distances in a 66 electron cluster framework.

The clusters are extremely stable as evidenced by their stability in air and the fact they may be vaporized intact in a mass spectrometer. Furthermore, they are soluble in common organic solvents and are relatively non-polar. It is this last property which renders these complexes especially suitable as precursors for highly dispersed, discrete cluster catalysts. Unlike ionic solutions of metal salts which tend to give uneven adsorption during the solvent removal on high surface area supports, these non-ionic complexes are extracted from the solvent phase by the support and form highly dispersed molecular entities on the surface. The following EXAMPLE I is presented to illustrate the catalyst preparation according to the present invention.

EXAMPLE I 0.25 grams of the FeMoS cluster composition, $Cp_2Mo_2Fe_2(\mu_3\text{-S})_2(\mu\text{-CO})_2(CO)_6$, formed and isolated from reaction (1) was dissolved in methylene chloride. To this solution was added 10.0 g of $\gamma$-alumina (225 m$^2$/g) previously calcined in oxygen at 500° C., to give a pink-brown, supported catalyst precursor containing 1.0% transition metal based on weight of Fe+Mo. The solvent was pumped off under reduced pressure and the solid dried under vacuum.

Figure 7:
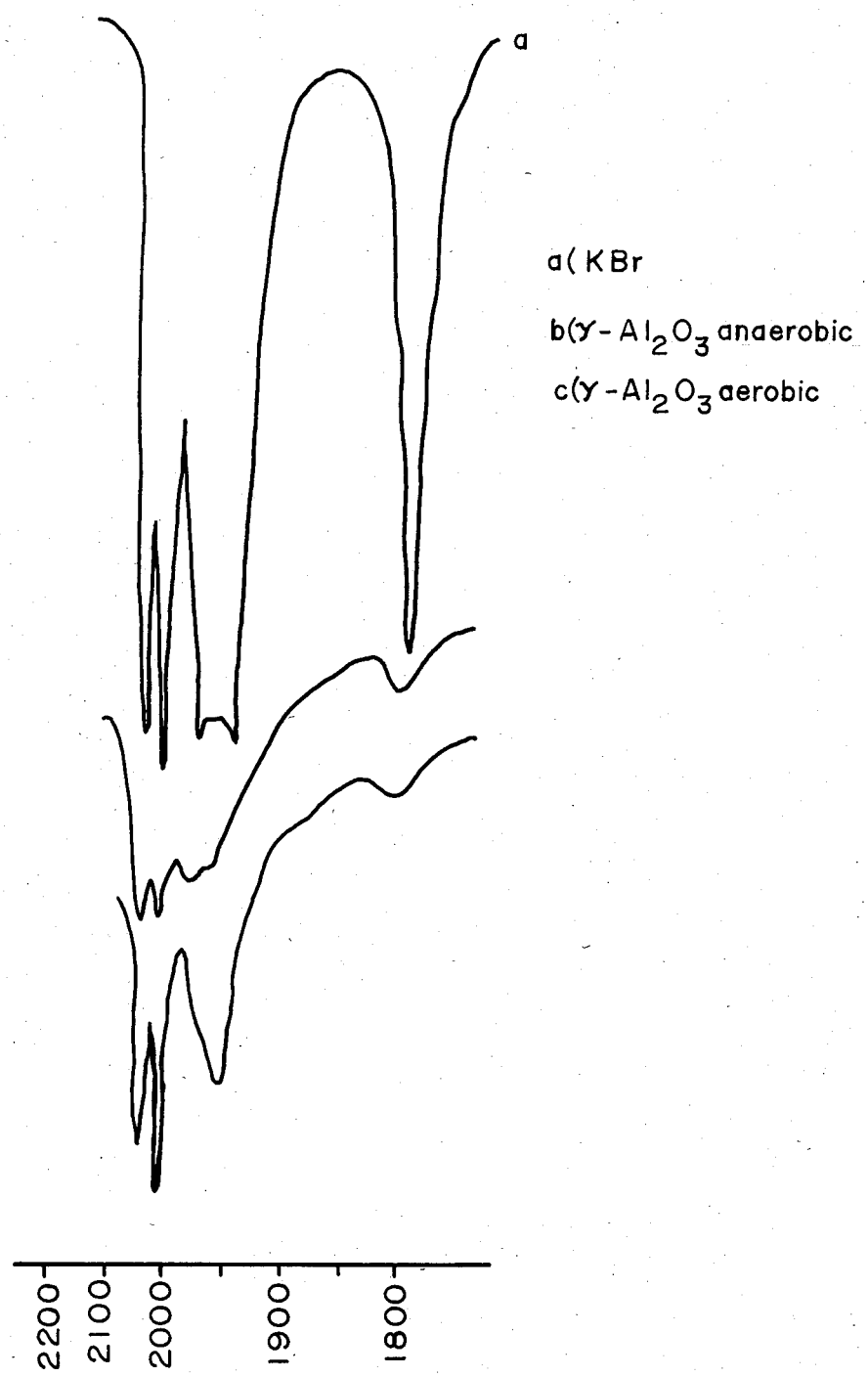
FIG. 7 illustrates the $\nu_{co}$ region of the IR spectra of the heterobimetallic clusters of FIG. 2 in KBr and on $\gamma$-alumina with and without exposure to air.

To confirm the presence of the stable cluster on the alumina support, IR spectra of the cluster in KBr, the cluster on $\gamma$-alumina without exposure to air and the cluster on the $\gamma$-alumina after exposure to air were measured. The $v_{co}$ region of the resulting IR spectra are presented in FIG. 7. As illustrated, these spectra demonstrate that the cluster absorbs on $\gamma$-alumina intact with little change in the basic structure of the cluster. Even the bridging carbonyl group ($v_{co}=1800$ cm$^{-1}$) is still present in the absorbed cluster.

EXAMPLE II

In order to illstrate the Temperature-Programmed Decomposition (TPD) step for activating the supported catalyst precursor according to the instant invention, a portion of the solid alumina with the deposited heterobimetallic cluster was placed in a flow reactor and activated by heating in a flow of $H_2$ at 400° C. at 1 atmosphere for 4 hours. The activated catalyst was then used in the flow reactor for catalysis studies.

EXAMPLE III

In order to demonstrate the catalytic CO hydrogenation process according to the present invention, activated catalyst of EXAMPLE II was contacted with a flowing mixture of hydrogen and carbon monoxide. The pressure ranged from 1 to 30 atmospheres while the temperature ranged from 100° to 500° C., preferably 240° to 300° C. The products were anlayzed by gas chromatography and mass spectral analysed. The products consisted of $CH_4$, $C_2H_6$, $CO_2$ and $H_2O$. Steady state activity was observed for periods of up to one week with minimal drop in activity (up to 5%). The original activity is readily restored by turning off the CO stream and contacting the catalyst with pure $H_2$ for short periods.

EXAMPLE IV

To further illustrate and exemplify the preparation of the supported bimetallic sulfide catalyst, a 1 weight % Mo+Fe catalyst supported on $\gamma$-alumina was prepared as follows. All operations were performed at ambient temperature (20° to 30° C.) unless otherwise specified.

Gamma alumina (92%, 8% $H_2O$, Strem Chemical) was pretreated under a dry $O_2$ stream at 500° C. for 12 hours, evacuated (0.1 mm Hg) for 1 hour and transferred to a storage flask under nitrogen.

A total of 20.37 g of treated alumina was transferred under nitrogen into a 250 ml round bottom flask with a stop cock sidearm. In a separate flask was weighed 0.503 g of $(CH_3C_5H_4)_2Mo_2Fe_2S_2(CO)_8$ (0.204 g of metal). The cluster was then dissolved under nitrogen atmosphere and transferred quantitatively on the alumina (slurried in 35 ml $CH_2Cl_2$) using a total of 50 ml $CH_2Cl_2$. The powder rapidly took on a red-brown color. The slurry was stirred for 30 minutes before the solvent was removed under vaccum (0.1 mm Hg). Vacuum was continued after solvent removal for 30 minutes. Samples were divided under nitrogen and sealed in glass ampules. The theoretical composition of the supported catalyst is 0.63% Mo, 0.37% Fe and 0.21% S

EXAMPLE V

In a manner analogous to EXAMPLE IV, the catalysts MoFe/$Al_2O_3$ and MoCo/$Al_2O_3$ were prepared and subsequently characterized before and after CO hydrogenation. The BET surface of both samples was about 150m$^2$/g and remained unchanged under reaction conditions. Electron microscopy was performed under high resolution (1.4Å lattice, 3Å point to point) using a top entry goniometer stage. The micrographs of both the fresh and used samples showed only the typical high-resolution fine structure of $\gamma$-$Al_2O_3$. No evidence of metal particles could be found. Since the identification of metal particles of 10 Å in diameter represent no problem under the high resolution condition employed in the microscope, it was concluded with confidence that the dispersion of the clusters remained high under the reaction conditions.

Additional characterization by scanning transmission electron microscopy, using a side-entry stage under normal resolution, coupled with X-ray energy dispersive spectroscopy was performed. This technique allows the analyzing of areas of 100 Å in diameter. Comparing the relative X-ray signal intensity of the Al with that of Fe, Co, or Mo verified that the clusters were uniformly distributed across the surface of the $Al_2O_3$ support.

Figure 8:
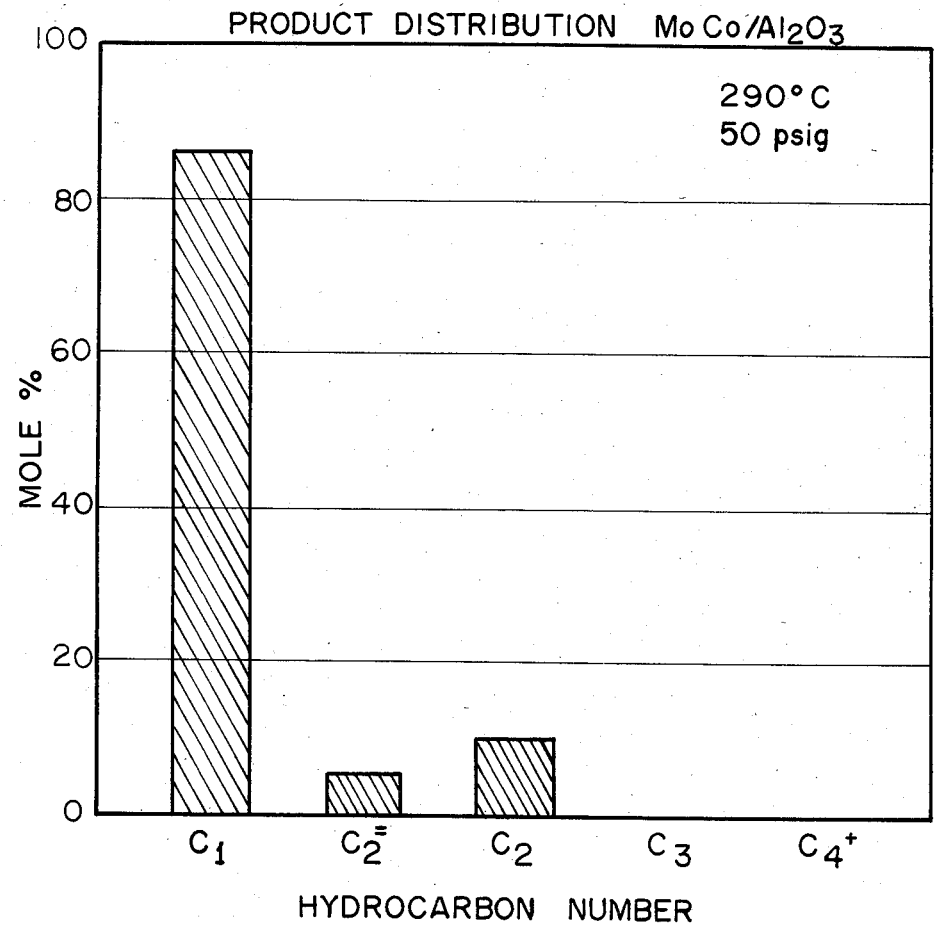
FIG. 8 illustrates the product distribution of the $CO+H_2$ hydrogenation reaction for the catalyst $MoCo/Al_2O_3$ according to the instant invention.

CO hydrogenation was carried out in a flow reactor at temperatures of 250° C. to 310° C. and the pressures of 2 to 10 atm. Both catalysts were pretreated in flowing H$_2$ at 400° C. for 4 hours. The initial activity for CO hydrogenation was low and increased steadily during the induction period lasting approximately 4 to 6 hours. This induction period was followed by a steady-state activity showing no significant deactivation over prolonged periods (up to 100 hours on stream). After regeneration in H$_2$, the catalysts followed the same reactivity patterns. On MoFe/Al$_2$O$_3$, the main hydrocarbon products were methane, and ethane, while on MoCo/Al$_2$O$_3$ the main hydrocarbon products were methane, ethylene and ethane as illustrated in FIG. 8. No C$_3$, C$_4$, C$_5$ or C$_7$+hydrocarbons were detected on either catalyst.

The advantages and benefits of the instant invention are considered to be numerous. The preparation of the novel bimetallic cluster catalysts, because of the fact the clusters are of known stoichiometry and initial structure, leads to distinct advantages over the prior art catalysts in terms of reproducibility of formulation and control over the nature and number of active sites. This in turn leads to greater certainty and understanding of the performance of the catalysts. The catalysts of the instant invention exhibit high dispersion of the active metals on refractory supports, high stability and reactivity under operating conditions as well as extraordinary ease of regeneration. An especially desirable advantage over the prior art is the highly selective formation of valuable hydrocarbons achieved with the instant invention. In particular, the novel catalysts provide for the reaction of hydrogen and carbon monoxide to form methane, ethane and no other hydrocarbon products.

The heterobimetallic cluster compositions of the present invention are not only specifically useful in hydrogenation catalysis of CO, but because of the presence of the sulfur and high activity and selectivity are generally envisioned as being particularly relevant to syngas conversion technology. In particular, it is generally known and accepted that both methanation catalysts based on Ni and the common Fischer-Tropsch catalysts are extremely sensitive to poisoning by sulfur in the syngas feedstream as are the ZnO/Cu methanol synthesis catalyst. The presence of a sulfide stabilized cluster represents a unique approach for providing a sulfur-tolerant catalyst. Thus, the catalytic processes according to the present invention are contemplated as being applicable to both direct liquefaction processes as well as syngas conversion.

Having thus described the invention with a certain degree of particularity, it is manifest that many changes may be made in the details without departing from the spirit and scope of this disclosure. It is understood that the invention is not limited to the exemplified embodiments set forth herein but is to be limited only by the scope of the attached claims, including the full range of equivalents to which each element thereof is entitled.

We claim:

1. The heterobimetallic cluster complex selected from the group consisting of Cp$_2$Mo$_2$Fe$_2$($\mu$-S)$_2$(CO)$_8$; Cp$_2$Mo$_2$Ni$_2$($\mu_3$-S)$_4$(CO)$_2$; Cp$_2$Mo$_2$Co$_2$($\mu_3$-S)$_2$($\mu_4$-S)(CO)$_4$; Cp$_2$Mo$_2$Fe$_2$($\mu_3$-S)$_4$(CO)$_6$ and Cp$_4$Mo$_2$Ni$_2$S$_4$ where Cp=$\eta^5$-C$_5$H$_4$R and R is —CH$_3$ or —H.

2. The heterobimetallic cluster complex of claim 1; Cp$_2$Mo$_2$Fe$_2$($\mu$-S)$_2$(CO)$_8$ where Cp=$\eta^5$-C$_5$H$_4$R and R is —CH$_3$ or —H.

3. The heterobimetallic cluster complex of claim 1; Cp$_2$Mo$_2$Ni$_2$($\mu_3$-S)$_4$(CO)$_2$ where Cp=$\eta^5$-C$_5$H$_4$R and R is —CH$_3$ or —H.

4. The heterobimetallic cluster complex of claim 1; Cp$_2$Mo$_2$Co$_2$($\mu_3$-S)$_2$($\mu_4$-S)(CO)$_4$ where Cp=$\eta^5$-C$_5$H$_4$R and R is —CH$_3$ or —H.

5. The heterobimetallic cluster complex of claim 1; Cp$_2$Mo$_2$Fe$_2$($\mu_3$-S)$_4$(CO)$_6$ where Cp=$\eta^5$-C$_5$H$_4$R and R is —CH$_3$ or —H.

6. The heterobimetallic cluster complex of claim 1; Cp$_4$Mo$_2$Ni$_2$S$_4$ where Cp=$\eta^5$-C$_5$H$_4$R and R is —CH$_3$ or —H.

7. The heterobimetallic cluster complex characterized by the formula:

$$Cp_2M_2M'_2S_x(CO)_n$$

wherein Cp=$\eta^5$-C$_5$H$_4$R and R is —CH$_3$ or —H and wherein M is a metal selected from the group consisting of Mo, W and V and wherein M' is a metal selected from the group consisting of Fe, Co and Ni and x and n are integers from about 2 to about 8.

8. A method of synthesizing Cp$_2$Mo$_2$($\mu$-S)$_2$($\mu$-SH)$_2$ consisting of the steps:
(a) Chemically reducing the polymeric sulfide (Cp$_2$Mo$_2$S$_x$)$_n$ dissolved in an organic solvent with a chemical reducing agent;
(b) quenching the reduction reaction by the addition of water;
(c) stripping the excess solvent and water; and
(d) recovering Cp$_2$Mo$_2$($\mu$-S)$_2$($\mu$-S)$_2$ wherein Cp=$\eta^5$-C$_5$H$_4$R and R is —CH$_3$ or —H.

9. A method of claim 8 further comprising the steps of washing the Cp$_2$Mo$_2$($\mu$-S)$_2$($\mu$-S)$_2$ with water and recovering purified Cp$_2$Mo$_2$($\mu$-S)$_2$($\mu$-S)$_2$.

10. A method of claim 9 wherein said organic solvent is THF and said chemical reducing is LiEt$_3$BH.

11. A method of preparing a molybdenum heterobimetallic cluster complex comprising the steps of:
(a) reacting Cp$_2$Mo$_2$($\mu$-S)$_2$($\mu$-SH)$_2$ where Cp=$\eta^5$-C$_5$H$_4$R and R=—CH$_3$ or —H with a group 8 metal carbonyl selected from the group consisting of Ni(CO)$_4$, Co$_2$(CO)$_8$, Fe$_2$(CO)$_9$ and Cp$_2$Ni$_2$(CO)$_2$; and
(b) recovering a heterobimetallic cluster composition selected from the group consisting of Cp$_2$Mo$_2$Ni$_2$($\mu_3$-S)$_4$(CO)$_2$, Cp$_2$Mo$_2$Co$_2$($\mu_3$-S)$_2$($\mu_4$-S) (CO)$_4$, Cp$_2$Mo$_2$Fe$_2$($\mu_3$-S)$_4$ (CO)$_6$ and Cp$_4$Mo$_2$Ni$_2$S$_4$.

12. A method of claim 11 wherein said group 8 metal carbonyl is Ni(CO)$_4$ and said heterobimetallic cluster complex is Cp$_2$Mo$_2$($\mu_3$-S)$_4$(CO)$_2$.

13. A method of claim 11 wherein said group 8 metal carbonyl is Co$_2$(CO)$_8$ and said heterobimetallic cluster complex is Cp$_2$Mo$_2$Co$_2$($\mu_3$-S)$_2$($\mu_4$-S)(CO)$_4$.

14. A method of claim 11 wherein said group 8 metal carbonyl is Fe$_2$(CO)$_9$ and said heterobimetallic cluster complex is Cp$_2$Mo$_2$Fe$_2$($\mu_3$-S)$_4$(CO)$_6$.

15. A method of claim 11 wherein said group 8 metal carbonyl is Cp$_2$Ni$_2$(CO)$_2$ and said heterobimetallic cluster complex is Cp$_4$Mo$_2$Ni$_2$S$_4$.

16. A method of preparing a heterobimetallic cluster complex comprising the steps:
(a) reacting Cp$_2$Mo$_2$(CO)$_4$ where Cp=$\eta^5$-C$_5$H$_4$R where R is —CH$_3$ or —H with Fe$_2$S$_2$(CO)$_6$; and
(b) recovering a heterobimetallic cluster composition Cp$_2$Mo$_2$Fe$_2$($\mu$-S)$_2$(CO)$_8$.

* * * * *